United States Patent [19]

Chen et al.

[11] Patent Number: 5,107,058
[45] Date of Patent: Apr. 21, 1992

[54] OLEFIN/PARAFFIN SEPARATION VIA MEMBRANE EXTRACTION

[75] Inventors: Tan-Jen Chen, Clearwater, Canada; James R. Sweet, Baton Rouge, La.

[73] Assignee: Exxon Research and Engineering Company, Florham Park, N.J.

[21] Appl. No.: 622,688

[22] Filed: Dec. 5, 1990

[51] Int. Cl.$^5$ .................... C07C 7/144; B01D 11/00
[52] U.S. Cl. ................... 585/818; 208/308; 210/644; 210/650; 210/651
[58] Field of Search ............ 585/818; 210/644, 650, 210/651; 208/308

[56] References Cited

U.S. PATENT DOCUMENTS

| | | | |
|---|---|---|---|
| 2,947,687 | 8/1960 | Lee | 210/23 |
| 3,043,891 | 7/1962 | Stuckey | 260/674 |
| 3,140,256 | 7/1964 | Martin et al. | 210/23 |
| 3,244,763 | 4/1966 | Cahn | 260/677 |
| 3,725,255 | 4/1973 | Barilli et al. | 208/331 |
| 3,725,256 | 4/1973 | Lugo et al. | 208/331 |
| 3,725,257 | 4/1973 | Cavenaghi et al. | 208/331 |
| 3,956,112 | 5/1976 | Lee et al. | 210/22 |
| 4,532,347 | 7/1985 | Vaughan | 562/528 |
| 4,551,156 | 11/1985 | Li | 55/16 |
| 4,586,939 | 5/1986 | Li | 55/16 |
| 4,614,524 | 9/1986 | Kraus | 55/16 |
| 4,670,151 | 6/1987 | Bitter et al. | 210/641 |
| 4,741,744 | 5/1988 | Wu et al. | 55/16 |
| 4,750,918 | 6/1988 | Sirkar | 55/16 |
| 4,780,114 | 10/1988 | Quinn et al. | 55/16 |
| 4,966,707 | 10/1990 | Cussler et al. | 210/632 |

FOREIGN PATENT DOCUMENTS

| | | |
|---|---|---|
| 1000432 | 1/1986 | Japan . |
| 3091122 | 4/1988 | Japan . |

OTHER PUBLICATIONS

"Microporous Membrane Solvent Extraction", Prasad, R., et al, Separation Science & Technology, 22(2 and 3), 619-640, 1987.
"Dispersion-Free Solvent Extraction with Microporous Hollow-Fiber Modules", Prasad, R., et al., AIChE Journal, Feb. 1988, vol. 34, No. 2, pp. 177-188.
"Designing Hollow-Fiber Contactors", Yang, M. C., et al., AIChE Journal, No. 1986, vol. 32, No. 11, pp. 1910-1916.
"Liquid-Liquid Extraction with Microporous Hollow Fibers", D'Elia, N. A. et al., J. Memb. Science 29 (1986), 309-319.
"Critical Entry Pressure for Liquids in Hydrophobic Membranes", Kim, B. S., et al., J. Colloid & Interface Science, vol. 115, No. 1, Jan. 1987, pp. 1-8.
"Solvent Extraction with Microporous Hydrophilic and Composite Membranes", Prasad, R., et al., AIChE Journal, Jul. 1987, vol. 33, No. 7, 1057-1066.
"Dispersion-Free Solvent Extraction with Microporous Hollow Fiber Modules", Prasad, R., et al., AIChE Summer National Meeting, Boston 1986.
"Nondispersive Solvent Extraction Using Microporous Membranes", Prasad, R. et al., AIChE Symposium, Membrane Materials & Processes, No. 261, vol. 84, 1988 (pp. 42-53).
"Hollow Fiber Solvent Extraction of Pharmaceutical Products: A Case Study", Prasad, R., et al., J. Mem. Sci. 47, 1989, 235-259.
"Novel Uses of Microporous Membranes: A Case Study", Callahan, R. W., AIChe Symposium Series, Membrane Materials & Processes, No. 261, vol. 84, 1988, pp. 54-65.

*Primary Examiner*—Anthony McFarlane
*Assistant Examiner*—Nhat Phau
*Attorney, Agent, or Firm*—Joseph J. Allocca

[57] ABSTRACT

Olefins are selectively separated from hydrocarbon feeds containing mixtures of olefins and paraffins by contacting said hydrocarbon feed mixture with one side of a micro-porous, non-selective partition barrier membrane while simultaneously passing, preferably in countercurrent flow, along the opposite side of said membrane a polar solvent. The olefin preferentially passes through said micro-porous non selective partition barrier in response to the polar solvent yielding a permeate enriched in olefin and a retentate enriched in paraffin as compared to the original feed stream.

7 Claims, No Drawings

OLEFIN/PARAFFIN SEPARATION VIA MEMBRANE EXTRACTION

BACKGROUND OF THE INVENTION

1. Field of the Invention

The present invention is a process whereby olefins are separated from hydrocarbon feeds containing mixtures of olefins and paraffins by the process comprising contacting said olefin/paraffin containing hydrocarbon feed with one face of a micro-porous, non-selective partition barrier membrane while simultaneously contacting the other face of said micro-porous, non-selective partition barrier membrane with a polar solvent, preferably in countercurrent flow. The olefins selectively permeate through the non-selective, micro-porous partition barrier membrane in response to the polar solvent on the permeate side of the partition barrier membrane resulting in the production of a permeate enriched in olefins and a retentate of reduced olefin content as compared to the original hydrocarbon feed.

2. Description of the Related Art

Nominally aliphatic hydrocarbon feedstocks contain various mixtures of paraffinic and olefinic hydrocarbons. Typical of such feeds is catalytic cracker off gas. Recovery of the olefinic component from these streams is of significant benefit insofar as rather than being burned as fuel the olefins can be employed in the manufacture of valuable chemicals and polymers.

Various processes have been suggested and described for olefin recovery.

In the NMP, N-methyl-2-Pyrrolidone Handbook published by the GAF Corporation the process of butadiene extraction is described.

In that process a feed of dilute $C_4$ hydrocarbons containing acetylenes is fed to the bottom of a first absorber after vaporization. Solvent absorbs the butadiene, all readily soluble components and part of the butenes In a rectification zone the butenes are stripped from the solvent by the ascending butadiene vapors. Hydrocarbons taken up in the NMP are removed in the stripper and returned by compressor to the rectification zone. Highly concentrated butadiene is withdrawn in vapor form from the lower half of the rectifier and washed with fresh NMP in a secondary absorber. $C_4$ acetylenes concentrate in the upper part of the stripper where they are removed with water vapor from the scrubbing of the solvent before recycle.

Because the olefins and paraffins of the same carbon number in the feed possess the same or essentially similar boiling ranges, separation by distillation is not possible.

The separation of hydrocarbons by type using selective membrane permeation has been described.

U.S. Pat. No. 2,947,687 and U.S. Pat. No. 3,043,891 disclose the separation of hydrocarbon mixtures by passing across the face of a non-porous membrane through which at least one component of the hydrocarbon mixture will permeate.

U.S. Pat. No. 3,043,891 teaches a process for increasing the permeation rate of saturated hydrocarbons through non-porous membranes which are capable of separating hydrocarbons according to type, and/or molecular configuration, and/or boiling point or molecular weight. The patent teaches that the permeation process is increased by contacting the membrane during the permeation process with an added hydrocarbon solvent for the membrane This solvent may contact the membrane on the feed side, the permeate side or on both sides. Representative of such permeation accelerating solvents include aromatics and unsaturated hydrocarbons such as olefins or diolefins. The solvent is described as being a solvent for the membrane i.e. swells the membrane.

The membranes employed are described as non-porous and include natural or synthetic rubber, gum rubber, chloroprene, neoprene, vinyl polymers such as styrene polymer, polyisobutylene, certain cellulose ethers.

The patent indicates that saturated molecules will permeate through the membrane in the following sequence of increasing selectivity: open chain highly branched hydrocarbons, < open chain with lesser degree of branching; < closed chain (e.g. cycloparaffins) and alkyl cycloparaffins, < straight chain or normal paraffins. Use of the membrane solvent will substantially increase the permeation without substantially altering the selectivity.

U.S. Pat. No. 2,947,687 teaches the separation of hydrocarbons by type through a non-porous membrane using a membrane solvent to enhance the permeation rate. Membrane solvents include substituted hydrocarbons which are soluble in and have solvent power for the membrane. The hydrocarbon solvent is an organic compound containing one or more atoms of halogen, oxygen, sulfur or nitrogen. Thus, materials such as carbon tetrachloride, alcohols, ketones, esters, ethers, carboxylic acids, mercaptans, sulfides (e.g. diethylsulfide etc.), nitropropane, nitrobenzene, acetonitrile, formamide, ethylene diamine, etc. may be employed in an amount ranging from 1 to 100% based on total solvent to hydrocarbon feed. The process may be operated at a pressure differential between the feed and permeate zone with the permeate being removed by vacuum. Alternately the permeate can be removed by a sweep stream such as steam, air, butane, etc.

The membrane is non-porous and includes natural or synthetic rubber, vinyl polymers, cellulose esters, cellulose ethers.

The process can use any hydrocarbon source as feed and permeation is in the order: saturated hydrocarbons, < unsaturated hydrocarbons, < aromatics. Saturated hydrocarbons of approximately the same boiling range permeate in the order: branched chain < cyclic chain < straight chain configuration, i.e. straight chain paraffins permeate more readily through the membrane. Olefins can also be separated from paraffins by this technique producing an olefins rich permeate.

In an example methyl cyclohexane is separated from an equal volume mixture of methyl cyclohexane and isooctane using 5% methyl ethyl ketone as solvent. An operating pressure differential of 400 mm Hg was maintained and the temperature was 52° C. and 82° C. The methyl cyclohexane preferentially permeated through the membrane.

U.S. Pat. No. 3,956,112 teaches a membrane solvent extraction process. The membrane solvent extraction system is utilized to separate two substantially immiscible liquids and extract a solute through a solvent swollen membrane from one solvent liquid phase to the extracting solvent liquid without direct contact between the liquid phases. The membrane is substantially non-porous Table III compares the invention of '112 with competing processes. One of these processes is described as direct extraction via porous partition. That process is practiced using two immiscible solvents The driving force is the chemical potential depending on the partition coefficient of the solute in the two solvents. The process employs a porous membrane or partition wall. In that process solutes from one solvent are transferred to the extraction solvent via direct solvent-solvent contact.

U.S. Pat. No. 3,140,256 teaches a membrane separation process employing a membrane comprised of a cellulose derivative (e.g. cellulose ester or ether) modified by reaction with aldehydes, organic di isocyanates, organic monoisocyanates, organo-phosphorus chlorides and organo-sulfur chlorides. Hydrocarbon feeds can be separated into their components by type using the membranes, e.g. aromatics can be separated from unsaturated hydrocarbons (olefins or di olefins) and/or from paraffins, or branched chain aliphatic hydrocarbons can be separated from other aliphatic hydrocarbons which have a different number of branched chains. Aromatic hydrocarbons permeate more rapidly than do the saturated (i.e. paraffins) hydrocarbons. In an example methyl cyclohexane permeated through the membrane more selectively than did iso octane.

"Microporous Membrane Solvent Extraction" Prasad, R., et al, Separation Science and Technology 22(2&3) 619–640, 1987 examines the phenomenon of dispersion-free solvent extraction through immobilized aqueous-organic interface in a microporous hydrophobic membrane. Expressly investigated was the use of an organic-organic interface to extract aromatics as exemplified by toluene, from a hydrocarbon feedstock, as exemplified by a mixture of toluene in n-heptane, employing a microporous Celgard 2400 polypropylene membrane to partition the feed from the polar extraction solvent, which in this case was NMP. The toluene selectively permeated through the porous Celgard membrane into the NMP thereby reducing the amount of toluene in the feed (raffinate) while increasing the amount of toluene in the permeate phase (extract).

SUMMARY OF THE INVENTION

Hydrocarbon feed mixtures of olefins and paraffins are separated by passing the feed mixture across one face of a non-selective, microporous partition barrier while simultaneously passing a polar solvent across the other face of said barrier whereby the olefins preferentially permeate through the partition barrier in response to the polar solvent present on the permeate side of the membrane resulting in an olefins rich permeate and an olefins lean retentate.

DESCRIPTION OF THE PREFERRED EMBODIMENTS

Hydrocarbon feeds containing mixtures of olefins and paraffins are separated into an olefin rich permeate stream and a paraffins rich retentate stream by the process of passing the hydrocarbon feed containing the olefins/paraffins mix across one face of a micro-porous, non-selective partition barrier membrane while simultaneously passing across the opposite face of said micro porous partition barrier membrane (preferentially in countercurrent flow) a polar solvent whereby the olefin component of the feed preferentially permeates through the porous partition barrier in response to the polar solvent passing along the opposite face of said membrane (i.e. the permeate zone).

The feed to the membrane separation process of the present invention is described as a hydrocarbon feed stream substantially comprising a mixture of olefins and paraffins, ranging from $C_2$ to hydrocarbon liquids with a final boiling point of 1050° F. Such streams occur as the products from various processes (e.g. cat cracking, steam cracking and coking) and recovery of the olefins from such streams provides valuable feedstock for other processes. The olefins separated from cat cracking and steam cracking is a feed source for alkylation reactions. The butenes and pentenes are feed source in the synthesis of MTBE and TAME. These other olefins can serve as feed source in the synthesis of alcohols, aldehydes, esters, and ethers.

The feed stream is passed along one side of a porous, non-selective partition barrier membrane. The barrier membrane can be described as being an ultrafiltration membrane and may be made of ceramic, sintered glass or metal or of a polymeric material such as polyethylene, polypropylene, teflon, nylon, cellulose, etc. and generally has a pore size in the range 100 to 5000Å. The membrane is preferably hydrophobic in nature.

The olefinic hydrocarbons selectively pass through this porous partition barrier in response to a polar solvent passing, preferably counter currently, along the opposite face of the barrier membrane. Examples of such polar solvents include aliphatic polyamines such as ethylene diamine, diethylene triamine or triethylene tetramine, phenol, furfural, sulfolane, dimethylsulfoxide (DMSO), N-methylpyrrolidone, acetonitrile and mixtures thereof.

In the present process, the feed and extraction solvent can be contacted at any temperature so long as both the feed and solvent are in the liquid state. Because the separation process is driven by the affinity of the polar solvent for the olefinic molecules, the process can be run at atmospheric pressure. Indeed, because of the high porosity of the membrane partition barrier the existence of a pressure differential, either by the direct application of pressure on the feed or solvent side or the creation of a vacuum on either side is undesirable as such a pressure differential would physically force feed or solvent across the barrier and thus defeat its purpose.

EXAMPLE

To illustrate the effectiveness of membrane extraction olefin/paraffin separation, a model compound feed mixture was used (50 LV% hexene and 50 LV% hexane). Celgard 2500 which is a micro-porous polypropylene membrane having oblong pores about 0.04×0.20 micrometers across was used to partition the olefin/paraffin mixture from DMSO which is a very polar solvent. Olefins preferentially permeate to the solvent side.

TABLE

| MEMBRANE EXTRACTION OLEFIN/PARAFFIN SEPARATION | | |
|---|---|---|
| Stream | Feed | Permeate |
| Membrane Extraction | | |
| Membrane | Celgard 2500 | |
| Solvent | DMSO | |
| Temperature, °C. | 53 | |
| Flux, kg/m$^2$/day | 29.9 | |
| Composition, LV % (1) | | |
| Hexane | 50.0 | 29.0 |
| 1-Hexene | 50.0 | 71.0 |

(1) Determined by FIA (Fluorescent Indicator Adsorption Test)

As can be seen from the table, the FIA data on the permeate and feed show that hexene/hexane separation was achieved. The feed has 50.0 LV% 1-hexene whereas the permeate has 71.0 LV% 1-hexene.

Although only data on hexene and hexane are shown herein, it is expected that the membrane separation described in this specification will be applicable to other olefins and paraffins. It is also expected that other polar solvents such as acetonitrile and sulfolane would be effective in olefin/paraffin separations. It is also expected that the separation can be extended to other micro-porous membranes such as teflon from Gore or nylon from Pall.

What is claimed is:

1. A method for separating olefins from hydrocarbon feed mixtures of olefins and paraffins, said method comprising contacting said hydrocarbon feed containing the mixture of olefins and paraffins in the liquid state with one face of a micro-porous, non-selective partition barrier membrane while simultaneously contacting the other face of said micro-porous, non-selective partition barrier with a polar solvent, in the absence of a pressure differential across the membrane, whereby the olefins in the feed selectively permeate through said microporous non-selective partition barrier in response to the polar solvent on the other side of the membrane resulting in a permeate enriched in olefins and a retentate of reduced olefin content as compared to the original hydrocarbon feed.

2. The method of claim 1 wherein the hydrocarbon feed comprises a mixture o f olefins and paraffins ranging from about $C_2$ to hydrocarbon liquids having a final boiling point of about 1050° F.

3. The method of claim 1 wherein the micro porous, non-selective partition barrier is an ultrafiltration membrane having a pore size in the range 100 to 5000Å.

4. The method of claim 3 wherein the micro porous, non-selective partition barrier is selected from ultrafiltration membranes made of polyethylene, polypropylene, teflon, nylon or cellulose.

5. The method of claim 1, 2, 3 or 4 wherein the polar solvent is selected from aliphatic polyamines, phenol, furfural, sulfolane, dimethylsulfoxide, N-methylpyrrolidone, acetonitrile and mixtures thereof.

6. The method of claim 5 wherein the polar solvent is ethylene diamine, diethylene triamine, or triethylene tetramine.

7. The method of claim 1, 2, 3 or 4 wherein the polar solvent contacted with the opposite face of the micro porous non-selective partition barrier membrane passes countercurrently across said membrane as compared to the direction of flow of the hydrocarbon feed.

* * * * *